United States Patent

Muller et al.

[11] Patent Number: 6,165,141
[45] Date of Patent: Dec. 26, 2000

[54] MEBSYSTEM

[75] Inventors: Bernd Muller; Peter Hartwig, both of Berlin; Uwe Dey, Falkensee; Bernd Sirozynski, Berlin, all of Germany

[73] Assignee: DMV Medizintechnik GmbH, Henningsdorf, Germany

[21] Appl. No.: 09/193,954

[22] Filed: Nov. 18, 1998

[30] Foreign Application Priority Data

Nov. 18, 1997 [DE] Germany .......................... 197 53 030

[51] Int. Cl.[7] .................................................. A61B 5/103
[52] U.S. Cl. ........................................ 600/587; 600/595
[58] Field of Search ................................... 600/587, 595

[56] References Cited

U.S. PATENT DOCUMENTS

| | | |
|---|---|---|
| 4,913,162 | 4/1990 | Leang et al. . |
| 5,496,450 | 3/1996 | Blumenthal et al. .................... 205/782 |
| 5,532,581 | 7/1996 | Ohkura et al. . |
| 5,828,197 | 10/1998 | Martin et al. ............................ 318/567 |
| 5,851,178 | 12/1998 | Aronow .................................. 600/323 |

FOREIGN PATENT DOCUMENTS

| | | |
|---|---|---|
| 35 41 649 A1 | 11/1985 | Germany . |
| 41 34 116 A1 | 4/1993 | Germany . |

*Primary Examiner*—Cary O'Connor
*Assistant Examiner*—Pamela Wingood
*Attorney, Agent, or Firm*—Barnes & Thornburg

[57] ABSTRACT

A measuring system is disclosed for the detection, the manipulation and the output of medical measured values which includes a computer, an input interface (2) for the connection of measuring probes (3, 4, 5), an output interface (6) for further manipulation of the measuring data detected by the measuring probes (3, 4, 5) as well as a signal output device (7), wherein the computer is connected to the input interface (2), the output interface (6) as well as to the signal output device (7). In addition, the computer includes a device for automatic recognition of a particular embodiment from a plurality of different predetermined embodiments of measuring probes (3, 4, 5) with the connection of a measuring probe (3, 4, 5) of a particular embodiment to the input interface (2) as well as a device connected therewith for reprogramming the computer as determined from the automatic recognition device.

33 Claims, 2 Drawing Sheets

MEBSYSTEM

The present invention relates to a measuring system for the detection, manipulation and output of medical measured values according to the preamble of the main claim.

Measuring systems for the detection, manipulation and output of medical measured values are well-known which include a computer, an input interface for the connection of measuring probes, an output probe for further manipulation of the measured data detected by the measuring probes as well as a signal output device, wherein the computer is connected to the input and output interfaces as well as to the signal output device. Mostly, such measuring systems are provided for more specific applications such as for the EMG measurement (electromyographic measurement) within the musculature of the human pelvic base. On that occasion, the restricted fields of application generally cause a low piece number of such measuring systems. Therefore, the price per piece becomes very high for such a measuring system. Frequently, such measuring systems are therefore present in greater doctor's surgeries or in hospitals only, and the long-duration observation of patients such as in an own flat is thus already made more difficult because of its costs. There is also the fact that several of the expensive measuring systems described above are required to allow a spectrum of various bodily functions to be checked wherein the rate of utilization of the single instruments is often low.

Therefore, the present invention is based on the object to provide a cost-effective measuring system which permits the measurement of different bodily functions in a simple manner.

This object is solved with a measuring system according to the preamble of claim 1 in combination with the characterizing features thereof.

As a result of providing the computer including a device for automatic recognition of a given embodiment from a plurality of various predetermined embodiments of measuring probes on connection of one measuring probe of a given embodiment to the input interface as well as a device connected therewith for reprogramming said computer as determined from the device for automatic recognition, the measurement of different bodily functions is possible with a single basic instrument. According to the bodily function to be measured merely a different embodiment of the measuring probe is connected to the input interface (a common characteristic feature of the measuring probes to preferably be used is in that they conclude the bodily functions from force measurements). The embodiment of the measuring probe is automatically detected, and the computer is accordingly reprogrammed such that a lavish calibration does not apply which often can only be performed with great professional qualifications. Reprogramming may take place, for example, such that a predetermined measuring programme is polled. Thus, for example, it is possible for low technically skilled persons as well to reprogram the instrument for the respective problem definition in the shortest time (simply by changing the measuring probe). Advantageous improvements of the present invention are indicated in the dependent claims.

An advantageous improvement intends to output a signal by the signal output device with reaching a predetermined limiting value detected by the measuring probe, and/or the signal output device is constructed as a LCD display or an acoustic signal transmitter. With this improvement the measuring system can be constructed as a "biofeedback" system. Hence, for the patient a simple check of bodily functions is enabled. Thus, the patient may check the tone of the pelvic base musculature, for example, in a very simple manner which is measured with a suitable measuring probe. The "biofeedback" system indicates whether the right muscle is exerted at all by the patient and whether the strain exceeds a desired limiting value. A direct control of the measured data by means of the LCD display promotes correct performing of the trainings. An active patient's participation in a predetermined training programme increases the awareness for the specific problems with restoring and conservation such as the musculature of the pelvic base, and may contribute in this way to an increase of a long-term success rate. A further advantageous embodiment provides for the measuring probe to be constructed as a rectal or vaginal probe to measure the radial forces for an operational check of the musculature of the human pelvic base. The musculature of the pelvic base is a very complex network of groups of muscles including inter alia two anus sphincters as well as a muscle in the bladder outlet. The condition of the above mentioned sphincters and the entire pelvic base musculature, respectively, can be concluded from radial forces affecting the rectal or vaginal probes according to the invention. In comparison with conventional methods for measuring these muscle groups such as by means of the electromyographic measurement (EMG) a direct detection of the muscle forces to be measured is enabled, while with the EMG method having electrodes fastened to the muscles (generally surface electrodes) only potentials of activated muscles are measured. With a direct force measurement there are distinctly less sources of error than with the EMG method, in which such as contaminations or different skin thicknesses have a decisive influence on the measuring results.

A further advantageous embodiment provides the rectal or vaginal probe to comprise a substantially rigid basic body, a shifting portion which is movable substantially radially toward the inserting direction as well as at least a force sensing element located between the basic body and the shifting portion which is connectable to the input interface. With this embodiment the construction of the probe is very simple, in addition with the used force sensing element it may be fallen back to component parts whereby the costs of the rectal and vaginal probe are decisively reduced.

A particularly advantageous embodiment provides the measuring probe to be constructed as a probe for sensing the urine flow and/or detecting the amounts of stool, and includes an impact surface suspended from at least three locating means. It is particularly advantageous that the probe for sensing the urine flow and/or detecting the amounts of stool comprises a force measuring element detecting the tensile force within a locating means. With such a device on impacting a jet of urine immediately directed upon the impact surface the volume flow of the jet of urine can be determined through the tensile force to be measured within one of the locating means. The locating means according to the invention (for example hooks or commercially available scotch tapes or suction cups as well) allow the probe for sensing the urine flow and/or detecting the amounts of stool to be installed in one movement in the home toilet. Storing the measured data enables later analysis in a doctor's surgery or in a hospital. With the application of the inventory probe for sensing the urine flow and/or detecting the amounts of stool extensive data may be collected enabling the control of progression under natural conditions. This includes a control of progression with the application of new medicines for prostate patients or after an operation of the prostate, for example. In addition, detecting and recording the amounts of stool is possible. In each case, it is advantageous to form the impact surface from a water-soluble material such that the impact surface after being used can be flushed down inside the toilet without any considerable environmental pollution.

A particularly advantageous improvement provides the measuring probe to be constructed as a probe for penile rigidity. Here, it is favourable that the probe for penile rigidity being advantageously configured as a circumferentially flexible slip-on penis ring comprises two naps lying upon another with respect to the longitudinal penis axis, wherein a device is provided which prevents a relative motion of the naps to each other in the circumferential direction of the penis, and that the naps are engaged respectively with one end of a flexible tape in such a manner that the superimposed naps form a ring together with the flexible tape, and the superimposed naps are forced against each other on an elastic expansion of the ring from the inside. With a force sensing element which is located between the superimposed naps the penile rigidity can be concluded from an outwardly directed radial pressure exerted by the penis upon the ring. With this, unlike the prior art, a particularly simply constructed probe for penile rigidity is provided which can be adjusted to the respective penis by means of flexible tapes having a different length and limberness. In addition, the force-sensing element disposed between the two superimposed naps comprises a defined seat between the two substantially rigid naps. In contrast to well-known devices the probe for penile rigidity is substantially restricted to the measurement of the penile rigidity, since this represents the essential proportion to practise sexual intercourse. The diameter increase being additionally measured with prior art devices is admittedly possible as well with the present invention (by means of a well-known force-displacement relation of the flexible tape) but is not required. Thus, the present invention provides a very simple system for rigidity measurement and hence for the diagnosis of impotence. For example, measurements of rigidity can be performed and recorded during the night's sleep of a patient by applying the probe for penile rigidity, since in this manner it may be concluded therefrom between physiological and psychological causes of impotence. This differentiation which is possible with devices according to the prior art only including very expensive instruments (for example such ones which are available in bedroom labs of hospitals, but here there are very long waits) can be carried out now in a more cost-effective manner. Thus, for example, a registered doctor may give the measuring equipment to the patient for carrying home whereby substantial costs for a stay in clinic can be saved for the moment, and in addition the measuring result is not falsified by virtue of influence of the unused environment.

A particularly advantageous embodiment provides for the measuring system to include two input interfaces and for the computer to include a device for simultaneously detecting two measuring probes connected to the input interfaces. Therewith, it will be enabled to detect complex interrelationships between different bodily functions which is only possible in the prior art with a very expenditure of instruments. Thus, with the measuring system according to the invention a complex diagnosis of bladder weakness and urinary tract deseases, respectively, can be performed, for example, with the parallel use of a probe for sensing urine flow and/or detecting amounts of stool as well as a rectal or vaginal probe for measuring the musculature of pelvic base. In addition, with applying a probe for penile rigidity during the night's sleep of a patient an electoencephalogram can be prepared or the pulse frequency can be detected through a second input interface in order to be able making such statements about the respective sleeping phase of the patient and performing a safer diagnosis.

Further advantageous embodiments are indicated within the remaining dependent claims.

The inventory measuring system is explained now according to figures in which.

Figure 4A:
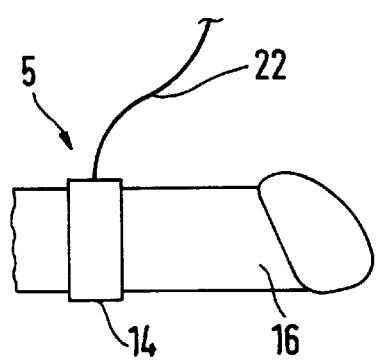
Figure 4B:
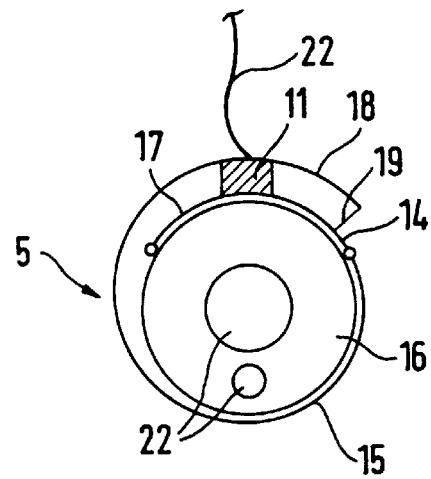

FIG. 4a and FIG. 4b probes according to the invention for penile rigidity.

Figure 1:
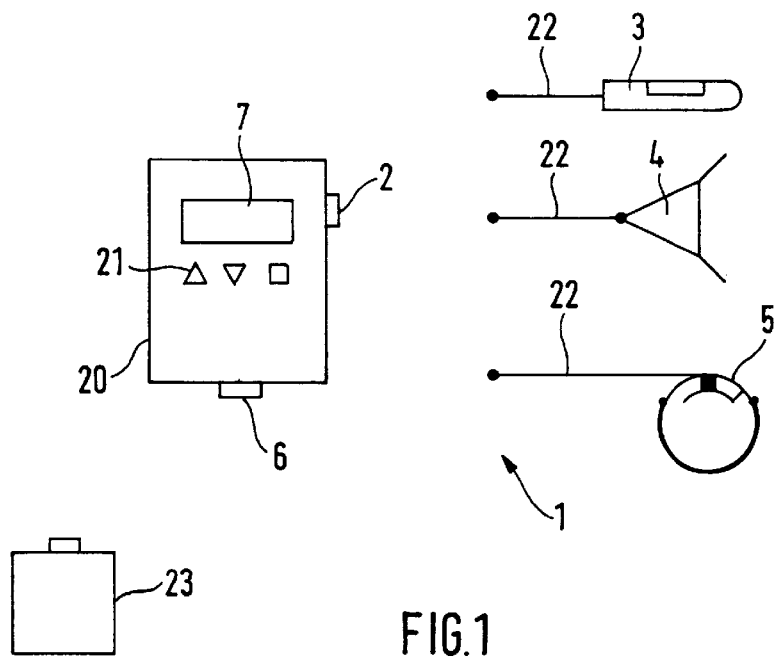
FIG. 1 shows a measuring system according to the invention.

FIG. 1 shows a measuring system 1 according to the invention.

A basic instrument 20 includes a computer which is not shown in more detail. This computer is connected to an input interface 2 for the connection of the force-sensing measuring probes 3, 4, 5 and to an output interface 6 for a further manipulation of the measuring data detected by the measuring probes 3, 4, 5. In addition, the basic instrument 20 comprises a signal output device 7 which is constructed as a LCD display in the present case. The signal output device 7 which can also be constructed as an acoustic signal transmitter, for example, is connected to the computer as well. The computer additionally includes a device for the automatic recognition of a particular embodiment from a plurality of different predetermined embodiments of measuring probes 3, 4, 5 with the connection of a measuring probe 3, 4, 5 of a particular embodiment to the input interface 2. These various embodiments may represent a measuring probe constructed, for example, as a rectal or vaginal probe 3, a measuring probe constructed as a probe for sensing the urine flow and/or for detecting the amounts of stool 4 or a measuring probe constructed as a probe for the penile rigidity 5. These probes output electric signals to the input interface 2. In suitable sensors which are constructed as force-sensing elements, for example, the measured forces are converted into electric signals, and the measured variables are transmitted to the computer in this way through the lines 22 when connected to the input interface 2. The input interface 2 is a coded interface (when the measuring probes 3, 4 or 5 are connected the computer detects which embodiment of a measuring probe is dealt with). In addition, the computer includes a computer reprogramming device which is connected to the device for automatic detection. According to the selected embodiment of the measuring probe (for example is selected the embodiment as a probe for sensing the urine flow and/or detecting the amounts of stool) the computer adapts the operation mode of the measuring system to the selected embodiment of the measuring probe. This includes an automatic calibration as well as a display of appropriate instructions on the LCD display 7. A manual intervention into the service and a variation of operational parameters is possible by means of the control buttons 21. In addition, it may be provided that a data storage element (such as an EEPROM or a Flash-EPROM belonging to the measuring probe is to be read out. In this data storage element being not shown in the figures correction data may be filed which can be read out after connection to the basic instrument 20 and taken into consideration by the computer with measurements and records. The basic instrument 20 is characterized by its handiness. Therefore, it is easily enabled to transport the entire measuring equipment in order to carry out measurements in the patient's flat. The computer contained in the basic instrument 20 advantageously comprises a great working memory for storing measured data measured over a long time period. Of course, with particularly long series of measurement it is also possible to use magnetic data carriers such as cassettes or floppy disks. However, in each case it is possible for the patient to remain in his usual home milieu, and that the data collected over a longer time may be fetched later through an output interface 6 and can be further processed. With this, for storing, processing and printing the measured data such an output interface can be provided with a data reader 23 or a conventional personal computer being connected to a printer.

Figure 2:
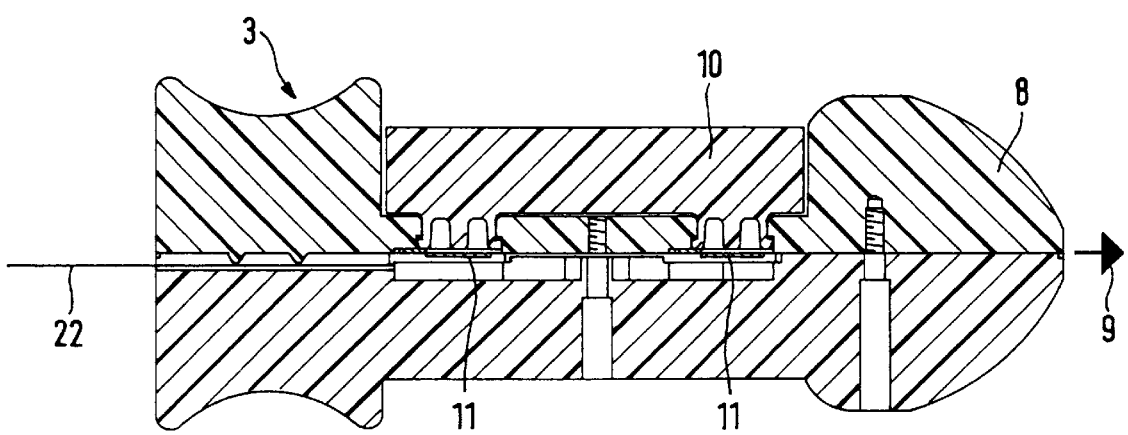
FIG. 2 shows a rectal or vaginal probe according to the invention.

FIG. 2 illustrates a rectal or vaginal probe 3 according to the invention, wherein a rectal probe according to the invention differs from a vaginal probe according to the invention only by its dimension. Such a measuring probe is primarily used for operational check and specific training of the pelvic base musculature. The musculature of the pelvic base includes inter alia two anus sphincters (an inner sphincter and an outer sphincter being further located toward the body outside) as well as a muscle on the bladder outlet which is essential for conscious opening and closing the bladder. In particular, with patients suffering from an incontinentia (for example caused by nervous damages or also as a result of old age) operational check of the pelvis base musculature as well as specific training of this musculature are desirable. Both can be insured with the rectal or vaginal probe according to the invention. With this, the rectal or vaginal probe is inserted into the anus and into the vagina, respectively. In the present embodiment the rectal or vaginal probe 3 comprises a basic body 8 which is substantially rigid and can be manufactured from an appropriate plastic, for example. This basic body comprises a substantially circular cross-section and has a lead-in bevel on the tip thereof in the inserting direction 9 as well as a suitable handle on the opposite end. In addition, the rectal or vaginal probe 3 has a shifting portion 10 being movable in the radial direction. The force-sensing elements 11 are disposed between the basic body 8 and the shifting portion 10. These are suitable to perform the measurement of radial forces. In the inserted condition such forces are applied by the sphincters mentioned above. The force-sensing elements 11 are common elements to sense forces (wire resistance strain gauge principle) which conclude the applied force from the displacement path of the shifting portion 10 (the relation between force and deformation of the force-sensing elements is well-known). The present embodiment illustrates an arrangement having two force-sensing elements lying one after another in the inserting direction 9. For example, with measurements inside the anus it is possible therewith to separately detect the muscle forces of the inner and outer sphincters. Of course, it is also possible, however to configure one embodiment of the rectal or vaginal probe 3 according to the invention with merely one force-sensing element. Such force-sensing elements transmit the measured data in the form of electric pulses to the input interface 2 through a line 22. With the present vaginal or rectal probe a rapid diagnosis may be made about closing muscle forces, and in addition it is also possible to provide a "biofeedback" system wherein the muscles can be trained. Here, the muscles of the patient have to be strained such that a predetermined limiting value is achieved by the force-sensing elements 11. With reaching these predetermined measured value the signal output device 7 outputs a signal such as in the form of signs of the LCD display or acoustic signal transmitter. Therewith, it is possible for the patient to learn straining the right muscles, in addition, the time development of the training condition is detectable by means of storage devices included in the computer.

Figure 3A:
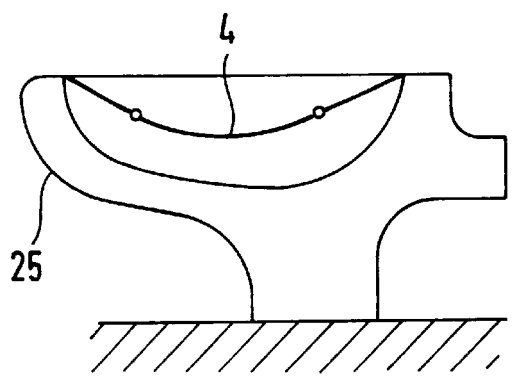
FIG. 3a and FIG. 3b show a probe for sensing urine flow and/or detecting amounts of stool according to the invention which is hung up in a toilet.
Figure 3B:
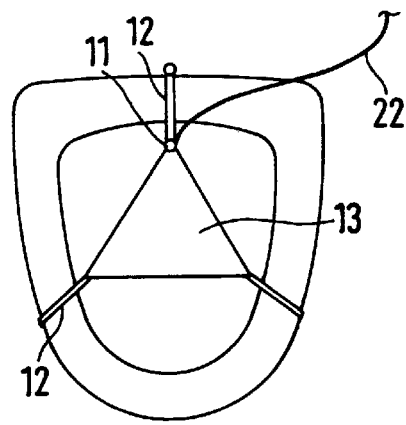

FIG. 3a shows the side view of a probe for sensing urine flow and/or detecting amounts of stool 4 which probe is clamped in the coventional toilet 25. A top view of the clamped probe for sensing urine flow and/or detecting amounts of stool 4 is seen in FIG. 3b. Here, it is a matter of an impact surface 13 suspended from three locating means 12. At one of the locating means a force-sensing means 11 is disposed such that it detects the tensile force within the locating means 12. The locating means can be constructed as scotch tapes glued on the toilet rim or as suction cups being detachable on the toilet surface. Of course, it is also possible to use suitable hooks therewith. With impacting a urine jet upon the impact surface 13 a tensile force originates within the locating means 12 which is detected by means of the force-sensing element 11. In an analogous manner with regard to the force-sensing elements described above the measuring result is transmitted in the form of electric pulses through a line 22 to the input interface 2. The volume flow of the urine jet can be concluded from the amount of the measured tensile force. Therewith, applicable conversions are performed in the computer. Of course, a "biofeedback" system is enabled with such a probe for sensing urine flow and/or detecting amounts of stool. With this, the volume flow of the urine jet can be measured as with human beings suffering from a prostate condition, and a respective optical or acoustic signal can be outputted by the signal output device 7 if a predetermined limit is exceeded. With a probe for sensing urine flow and/or detecting amounts of stool according to the invention it is also possible to define the amounts of stool (the weight of the amount of stool to be determined is defined via the tensile force detected by the force-sensing element 11 within the locating means 12). By virtue of the material of the impact surface 13 since it is composed of a water-soluble material the impact surface 13 can be easily disposed in the toilet.

FIG. 4a illustrates a penis 16 comprising the placed measuring probe for the penile rigidity 5. The probe for penile rigidity includes a ring 14 detachable upon a penis 16. FIG. 4b shows a cross-section taken along a penis 16 having erectile organs 24 (corpora cavernosum penis). A detachable ring 14 is disposed around the penis. In the circumferential direction the ring 14 includes flexible sections 15 which are constructed as flexible tapes. In addition, the probe for the penile rigidity comprises two naps 17, 18 lying one upon another with regard to the longitudinal axis of the penis 16. A device for preventing a relative motion 19 is also provided which prevents a relative motion of the naps to each other in the circumferential direction of the penis. This device for preventing a relative motion 19 can be constructed in various manners for example by simply hanging up. One end of the flexible tape 15, respectively engages the superimposed naps 17 and 18 lying one upon another in such a manner that with swelling up the erectile organs 24 and thus the entire penis 16 in the circumferential direction, the superimposed naps 17 and 18 are pressed together in the radial direction. The force originating at the same time is received from a force-sensing element 11 in the manner outlined above and the measured measuring data are transmitted in the form of electric pulses through a line 22 to the input interface 2. With this device the measurement of the penile rigidity is prominent since the rigidity is the crucial factor with the male impotence. However, it is also possible with the present probe for penile rigidity to detect a tumescence (increase of circumference). This is easily enabled with the knowledge of the relation between force and deformation of the flexible tape 15. This relation between force and deformation has to take account of nonlinearities based on the geometric proportions with tape deformation as well as nonlinearities of the spring characteristic. Information about these nonlinearities can be stored within a data storage element (for example an EEPROM or a Flash-EPROM). This data storage element can be directly fixed to the ring 14 and may include further information for a calibration of the probe for penile rigidity. This information is then read out while connected to the input interface, and is taken into consideration with the measurement and recording of measured data. The force-sensing element 11 is to be configured such that it is allowed to detect measurements of forces up to 6 Newton (in the normal case, however, the measuring range does not exceed over 4.5 Newton). It all depends on whether a rigidity or tumescence measurements of the penis are prominent the spring characteristic of the flexible tape can be accordingly selected. For the rigidity measurement it is sufficient to provide a relatively stiff against extension flexible tape 15. Moreover, it is sufficient with correct adapting the probe for penile rigidity to construct the force-sensing element 11 as a micro switch, for example, which transmits a signal to the computer with exceeding a predetermined limiting value. In addition, this embodiment is particularly cost-saving. If a measurement of tumescence is to be performed, it is advantageous to provide a less extension-proof material for the flexible tape 15, since here the penis will not be deformed (contracted). This contraction is absolutely to be avoided, since incorrect measuring values are detected otherwise. While the rigidity measurement merely matters the absolute value of the forces originating from the radial extension of the penis (the flexible tape 15 merely serves for load transmission) while tumescence measurement matters the right alternation of length of the flexible tape. The circumference of the penis is concluded from this alternation of length. Hence, it is important that the flexible tape possibly acts a few radial forces upon the penis, such that the penis circumference at the measuring point is approximately the circumference which the penis would comprise when the ring 14 was not installed on this location. Of course it is also possible to simultaneously dispose two rings 14 on the penis measuring the rigidity at different locations of the penis or to separately detect the rigidity and increase of circumference as well.

The probe for penile rigidity 5 is particularly suitable to be applied during the night's sleep of the patient. During the night's sleep the patient passes different sleeping phases. During the REM (Rapid Eye Movements) phases formation of rigid penis takes place with a healthy patient. This characteristic feature is most important for the exploration of impotence, since it permits a discrimination of somatic and psychological impotences. A patient comprising the phenomenons of impotence merely in a state of wakefulness but still forms a rigid penis during REM phases suffers from a psychological impotence while a patient which does not form a rigid penis during the REM phases as well suffers from a somatic impotence. The simple and cost-effective construction of the measuring system also permits a simple handling outside the clinic and thus being suitable for the application by registered doctors, sex therapeutists and particularly by patients at home.

In another embodiment the measuring system according to the invention comprises two input interfaces 2, and the computer also comprises a device for simultaneously detecting two measuring probes 3, 4 and 5 connected to the input interfaces 2. Therewith it is possible to illustrate certain correlations between the measured values supplied from the single different measuring probes. For example, it is possible to determine the interrelationship between the function of bladder sphincter and the volume flow of an urine jet. This allows to make the diagnosis distinctively safer both with sphincterial insufficiency and prostate pains as well. In addition, with application of a probe for penile rigidity during the night's sleep of a patient, for example, an electroencephalogram is prepared or pulse frequency is detected through a second input interface in order to make statements about the respective sleeping phase of the patient. Thus, according to the characteristic features of the electroencephalogram or pulse frequency measurement the REM phases can be concluded, and the penile rigidity can be simultaneously examined (with a single instrument) wherein the later diagnosis is decisively facilitated therewith.

What is claimed is:

1. Measuring system (1) for the detection, manipulation and output of medical measured values which comprises a computer, an input interface (2) to connect measuring probes (3,4,5), an output interface (6) for a further manipulation of measured data detected by the measuring probes (3,4,5) as well as a signal output device (7) wherein said computer is connected to said input interface (2), said output interface (6) as well as to said signal output device (7), characterized in that said computer includes a device for automatic recognition of a particular measuring probe (3,4,5) on connection of said measuring probe (3,4,5) to said input interface (2) as well as a device connected therewith for reprogramming said computer as determined from said automatic recognition device.

2. Measuring system as claimed in claim 1, characterized in that with reaching a predetermined limiting value detected by said measuring probe (3,4,5) from said signal output device (7) a signal is outputted.

3. Measuring system as claimed in claim 1 wherein said output interface (6) can be connected to a personal computer being connected to a printer for storing, processing as well as for printing the measured data.

4. Measuring system as claimed in claim 1 wherein said measuring probe is constructed as a rectal or vaginal probe (3) for an operational check of the musculature of the human pelvic base.

5. Measuring system as claimed in claim 4, characterized in that said rectal or vaginal probe (3) is constructed as a probe for sensing radial forces.

6. Measuring system as claimed in claim 5, characterized in that said rectal or vaginal probe (3) comprises a substantially rigid basic body (8), a shifting portion (10) substantially radially movable toward the inserting direction (9) as well as at least a force-sensing element (11) between said basic body (8) and said shifting portion (10) which said force-sensing element (11) can be connected to said input interface (2).

7. Measuring system as claimed in claim 4 wherein said rectal or vaginal probe (3) comprises a substantially circular cross-section in the inserting direction (9) and has a lead-in bevel on the tip thereof.

8. Measuring system as claimed in claim 1 wherein said measuring probe is constructed as a probe for sensing the urine flow.

9. Measuring system as claimed in claim 8, characterized in that said probe for sensing the urine flow (4) includes an impact surface (13) suspended from at least three locating means (12).

10. Measuring system as claimed in claim 9, characterized in that said probe for sensing the urine flow comprises a force-sensing element (11) detecting the tensile force within said locating means (12).

11. Measuring system as claimed in claim 9 wherein said impact surface (13) is composed of a water-soluble material.

12. Measuring system as claimed in claim 1 wherein said measuring probe is constructed as a probe for the penile rigidity (5).

13. Measuring system as claimed in claim 12, characterized in that said probe for the penile rigidity (5) includes a ring (14) detachable on the penis (16), which ring comprises flexible sections (15).

14. Measuring system as claimed in claim 13, characterized in that said probe for penile rigidity (5) comprises two naps (17, 18) lying upon another with respect to the longitudinal axis of the penis (16), wherein a device being provided to prevent a relative motion (19) of said naps (17, 18) to each other in the circumferential direction of the penis, and that said naps (17, 18) are each engaged with one end of a flexible tape (15) in such a manner that said superimposed naps (17, 18) together with said flexible tape (15) form a ring (14), and said superimposed naps (17, 18) are forced against each other on the elastic expansion of said ring (14) from the inside.

15. Measuring system as claimed in claim 14, characterized in that it includes a force-sensing element (11) between said superimposed naps (17,18).

16. Measuring system as claimed in claim 1 wherein said system includes two input interfaces (2), and that said computer includes a device for simultaneously detecting two measuring probes (3,4,5) connected to said input interfaces (2) and said one measuring probe (3,4,5), respectively, as well as an additional measuring means for pulse measurement, electroencephalogram type detection as well as the measurement of breathing frequency.

17. Measuring system as claimed in claim 1 wherein said signal output device is constructed as a LCD display (7).

18. A measuring system as claimed in claim 17 wherein said output interface (6) can be connected to a personal computer being connected to a printer for storing, processing as well as for printing the measured data.

19. A measuring system as claimed in claim 17 wherein said measuring probe is constructed as a rectal or vaginal probe (3) for an operational check of the musculature of the human pelvic base.

20. A measuring system as claimed in claim 18 wherein said measuring probe is constructed as a rectal or vaginal probe (3) for an operational check of the musculature of the human pelvic base.

21. Measuring system as claimed in claim 19, characterized in that said rectal or vaginal probe (3) is constructed as a probe for sensing radial forces.

22. Measuring system as claimed in claim 20, characterized in that said rectal or vaginal probe (3) is constructed as a probe for sensing radial forces.

23. A measuring system as claimed in claim 1 wherein said signal output device is constructed as an acoustic signal transmitter.

24. A measuring system as claimed in claim 23 wherein said output interface (6) can be connected to a personal computer being connected to a printer for storing, processing as well as for printing the measured data.

25. A measuring system as claimed in claim 23 wherein said measuring probe is constructed as a rectal or vaginal probe (3) for an operational check of the musculature of the human pelvic base.

26. A measuring system as claimed in claim 24 wherein said measuring probe is constructed as a rectal or vaginal probe (3) for an operational check of the musculature of the human pelvic base.

27. A measuring system as claimed in claim 25 wherein said rectal or vaginal probe (3) is constructed as a probe for sensing radial forces.

28. A measuring system as claimed in claim 26 wherein said rectal or vaginal probe (3) is constructed as a probe for sensing radial forces.

29. A measuring system as claimed in claim 2 wherein said measuring probe is constructed as a rectal or vaginal probe (3) for an operational check of the musculature of the human pelvic base.

30. A measuring system as claimed in claim 3 wherein said measuring probe is constructed as a rectal or vaginal probe (3) for an operational check of the musculature of the human pelvic base.

31. A measuring system as claimed in claim 29 wherein said rectal or vaginal probe (3) is constructed as a probe for sensing radial forces.

32. A measuring system as claimed in claim 30 wherein said rectal or vaginal probe (3) is constructed as a probe for sensing radial forces.

33. A measuring system as claimed in claim 1 wherein said measuring probe is constructed as a probe for detecting the amounts of stool (4).

\* \* \* \* \*